United States Patent

Lin et al.

[11] Patent Number: 6,014,223
[45] Date of Patent: Jan. 11, 2000

[54] METHOD OF DETERMINING THE IMPURITY CONCENTRATION OF IMPURITY-DOPED POLYSILICON IN SEMICONDUCTOR WAFERS

[75] Inventors: Jen-Tsung Lin, Taichung; Kuen-Chu Chen, Hsinchu Hsien; Keng-Yuan Wu, Kaoshiung; Eddie Chen, Hsinchu, all of Taiwan

[73] Assignee: United Microelectronics Corp., Hsinchu, Taiwan

[21] Appl. No.: 08/862,428

[22] Filed: May 23, 1999

[30] Foreign Application Priority Data

Mar. 13, 1997 [TW] Taiwan .................................. 86103098

[51] Int. Cl.$^7$ .................................................. G01N 21/55
[52] U.S. Cl. ............................ 356/448; 356/445; 356/446
[58] Field of Search ..................................... 356/445–448; 250/341.4, 341.8, 358.1; 117/85–86; 438/14–16; 364/468.28, 550, 570; 324/753

[56] References Cited

U.S. PATENT DOCUMENTS 4,564,761 1/1986 Buckwald et al. .................... 250/358.1
5,047,713 9/1991 Kirino et al. ............................ 324/752
5,705,403 1/1998 Baek et al. ................................ 117/85

FOREIGN PATENT DOCUMENTS 3-141659 6/1991 Japan .

*Primary Examiner*—Robert H. Kim
*Attorney, Agent, or Firm*—Finnegan, Henderson, Farabow, Garrett & Dunner, L.L.P.

[57] ABSTRACT

A method for determining the impurity concentration of impurity-doped polysilicon layers in semiconductor wafers is provided. Through experiments, it is found that the reflectivity of an impurity-doped polysilicon layer is nearly a regular function of the impurity concentration thereof. Accordingly, an impurity-doped polysilicon layer having an unknown impurity concentration can be determined by first measuring the reflectivity thereof by illuminating the impurity-doped polysilicon layer with light, and then using mapping transformation to find the corresponding value of impurity concentration of the impurity-doped polysilicon layer. This method can be used instead of the conventional thermal wave method that often result in having to discard the wafers due to the incapability of reliably determining the impurity concentration of the polysilicon layers formed on the semiconductor wafers.

4 Claims, 2 Drawing Sheets

METHOD OF DETERMINING THE IMPURITY CONCENTRATION OF IMPURITY-DOPED POLYSILICON IN SEMICONDUCTOR WAFERS

BACKGROUND OF THE INVENTION

1. Field of the Invention

This invention relates to semiconductor fabrication processes, and more particulary, to a method for determining the impurity concentration of impurity-doped polysilicon layers in a semiconductor wafer.

2. Description of Related Art

A semiconductor material, as the name implies, has electrical conductivity intermediate between that of a conductor and an insulator. One conventional method for increasing the conductivity of a semiconductor material, is to add an impurity material, called dopant, to the crystal structure of the semiconductor material to change the energy levels of its donors or acceptors. This forms a so-called extrinsic semiconductor whose electrical properties are dependent on the type and concentration of impurities added thereto. For instance, for silicon with a valence of 4, if an impurity material having a valence of 5, such as phosphorus, is added to the crystal structure of the silicon, the silicon will serve as an N-type semiconductor with increased conductivity due to an increased energy level caused by the presence of the impurity atoms.

By conventional inspection techniques, it is possible to ascertain whether an impurity-doped layer is adequately or inadequately doped with the impurity material because it can be checked by using a thermal probe, such as the Therma Probe 420 (TP420), to determine the current impurity concentration of the impurity-doped layer. In this method, a laser beam is produced by the thermal probe to illuminate the impurity-doped layer, and then the amount of thermal wave (TW) resulting from the illumination of the laser beam in the impurity-doped layer is measured. The detected TW value can be used to determine the impurity concentration of the impurity-doped layer.

The foregoing method, however, is only suitable for use on single-crystal silicon and not suitable for use on polysilicon. In an experiment, for example, five sample wafers formed with impurity-doped polysilicon layers are prepared. Then, the TW values of the impurity-doped polysilicon layers in these sample wafers are measured. The results are shown in Table 1.

From the data shown in Table 1, it is apparent that the TW values of the impurity-doped polysilicon layers display no regularity or repetitiveness. Consequently, it would be almost impossible to determine whether the impurity-doped polysilicon layers are adequately or still inadequately doped with the impurity material by checking on the TW values thereof. It is also impossible to determine the current impurity concentration of the impurity-doped polysilicon layers. Therefore, for an inadequately doped polysilicon layer, the compensation thereof can be carried out only by relying on an implantation data log (IMP. Data Log) recorded by the implantation machine, or on manually recorded data by the operating personnel. This practice is, of course, quite inaccurate. In the event of shutdown of the machine, software bugs, or failure to record data by the operating personnel, the whole wafer should be discarded since the impurity concentration of the impurity-doped polysilicon layers thereon is unknown.

Even if detailed and accurate records are available, the wafers that are formed with adequately doped polysilicon layers can be disorderly arranged due to malfunction of the sorter (a machine for sorting the wafers) or human error. This will preclude checking the wafers based on their TW values, resulting still in the necessity of discarding the wafers.

SUMMARY OF THE INVENTION

It is therefore a primary objective of the present invention to provide a method which can be used to determine the impurity concentration of impurity-doped polysilicon layers in semiconductor wafers.

In accordance with the foregoing and other objectives of the present invention, a new method for determining the impurity concentration of impurity-doped polysilicon layers in semiconductor wafers is provided. The method includes the following steps of:

(1) preestablishing the reflectivity versus impurity concentration characteristic for impurity-doped polysilicon;

(2) illuminating the impurity-doped polysilicon layer;

(3) measuring the reflectivity value of the impurity-doped polysilicon layer; and (4) using mapping transformation on the preestablished reflectivity versus impurity concentration characteristic to find the corresponding value of the impurity concentration.

BRIEF DESCRIPTION OF DRAWINGS

The invention can be more fully understood by reading the following detailed description, of the preferred embodiments, with reference made to the accompanying drawings and tables, wherein.

DETAILED DESCRIPTION OF PREFERRED EMBODIMENT

Through experiments, it is found that, for the polysilicon, the reflectivity values of both impurity-doped polysilicon layers and undoped polysilicon layers display high repetitiveness. In one experiment, five samples of impurity-doped polysilicon layers and another five samples of undoped polysilicon layers were prepared. Then, the reflectivity values of these samples were measured. The results are shown in Table 2.

It can be seen from Table 2 that the average reflectivity of the five samples of impurity-doped polysilicon layers is $0.4857 \pm 0.001$, and that of the five samples of undoped polysilicon layers is $0.6309 \pm 0.0035$. This result suggests that the reflectivity of an impurity-doped polysilicon layer is a nearly regular function of the impurity concentration thereof. Accordingly, it is concluded that an impurity-doped polysilicon layer having an unknown impurity concentration can be determined by first measuring the reflectivity thereof, and then using mapping transformation based on the reflectivity versus impurity concentration characteristic of the polysilicon to find the corresponding value of the impurity concentration.

A number of groups of sample wafers are thus prepared, each sample wafer being formed with one polysilicon layer that is doped with an impurity material in the ion implantation process at different energies in the range from 10 KeV (kiloelectronvolt) to 120 KeV. The energies of the impurity ions used in the ion implantation processes are divided into three ranges: a low-energy range, an intermediate-energy range, and a high-energy range. The impurity concentration ranges from $1 \times 10^{11}$ to $5 \times 10^{16}$ atoms/cm². The polysilicon layers on these sample wafers are doped with impurity material concentrations of 5%, 10%, 25%, 50%, 75%, and 100%, respectively.

The following three examples are based on the implantation of the impurity material into the various samples of polysilicon layers by conducting a low-energy ion implantation process, an intermediate-energy ion implantation process, and a high-energy ion implantation process, respectively.

EXAMPLE 1

(Low-energy Implantation)

In this example, five sample wafers, each being formed with one polysilicon layer thereon, were prepared. The polysilicon layers are doped with an impurity material to a concentrations of 0%, 25%, 50%, 75%, and 100%, respectively. Then, the TP420 thermal probe was used to measure the reflectivity of each of the five samples. The results are shown in Table 3.

Figure 1:
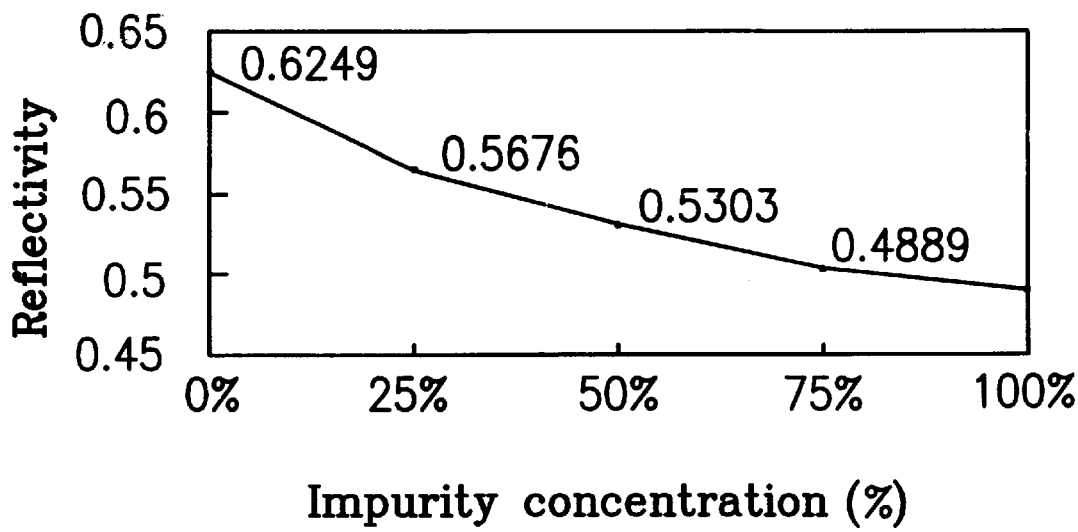
FIG. 1 is a graph, showing the reflectivity versus impurity dose characteristic of an impurity-doped polysilicon layer which is formed by a low-energy ion implantation process.

Based on the data shown in Table 3, the plot of the reflectivity versus impurity concentration characteristic is drawn and shown in FIG. 1. As shown, when the impurity material is doped by an low-energy ion implantation process, the reflectivity of the impurity-doped polysilicon is substantially a linear function of the impurity concentration.

Based on the plot of FIG. 1, a low-energy doped polysilicon layer having an unknown impurity concentration can be determined by first measuring the reflectivity thereof, and then using a mapping transformation to find the corresponding value of the impurity concentration on the horizontal axis.

EXAMPLE 2

(Intermediate-energy Implantation)

In this example, three sample wafers, each being formed with one polysilicon layer thereon, are prepared. Then, a series of intermediate-energy ion implantation processes are conducted on the sample wafers so as to dope an impurity material into the polysilicon layers on the sample wafers. The impurity concentrations of the doped polysilicon layers on the sample wafers are increased from 0% to 100% in steps, for example 0%, 5%, 10%, 25%, 50%, 75%, and 100%. The thermal-probe is used to measure the TW and reflectivity values of the polysilicon layers on these sample wafers. The results are shown in Table 4 and Table 5, in which Table 4 shows the TW values and Table 5 shows the reflectivity values of the polysilicon layers on the respective sample wafers.

It can be seen from Table 4 that the TW values indicate poor repetitiveness and regularity. By contrast, it can be seen from Table 5 that the reflectivity values indicate very good repetitiveness and regularity.

Figure 2:
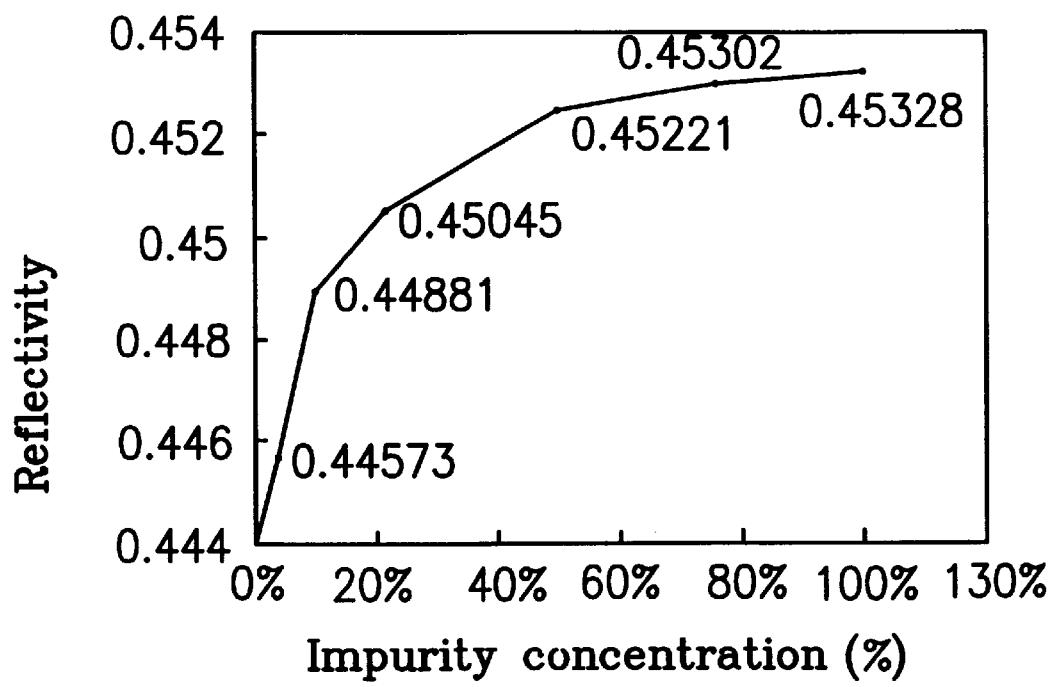
FIG. 2 is a graph, showing the reflectivity versus impurity dose characteristic of an impurity-doped polysilicon layer which is formed by an intermediate-energy ion implantation process.

Based on the data in Table 5, the plot of the reflectivity versus impurity concentration characteristic is drawn and shown in FIG. 2. As shown, when the impurity material is doped by an intermediate-energy ion implantation process, the reflectivity of the impurity-doped polysilicon is a curved function of the impurity concentration.

Based on the plot of FIG. 2, an intermediate-energy doped polysilicon layer having an unknown impurity concentration can be determined by first measuring the reflectivity thereof, and then using mapping transformation to find the corresponding value of impurity concentration on the horizontal axis.

EXAMPLE 3

(High-energy Implantation)

In this example, three sample wafers, each being formed with one polysilicon layer thereon, are prepared. Then, a series of high-energy ion implantation processes are conducted on the sample wafers so as to dope an impurity material into the polysilicon layers on the sample wafers. The impurity concentrations of the doped polysilicon layers on the sample wafers are increased from 0% to 100% in steps, for example 0%, 5%, 10%, 25%, 50%, 75%, and 100%. The thermal-probe is used to measure the TW and reflectivity values of the polysilicon layers on these sample wafers. The results are shown in Table 6 and Table 7, in which Table 6 shows the TW values and Table 7 shows the reflectivity values of the polysilicon layers on the respective sample wafers.

It can be seen from Table 6 that the TW values indicate poor in repetitiveness and regularity. By contrast, it can be seen from Table 7 that the reflectivity values indicate very good repetitiveness and regularity.

Based on the data in Table 7, the plot of the reflectivity versus impurity concentration characteristic is drawn and shown in FIG. 2. As shown, when the impurity material is doped by a high-energy ion implantation process, the reflectivity of the impurity-doped polysilicon is a curved function of the impurity concentration.

Figure 3:
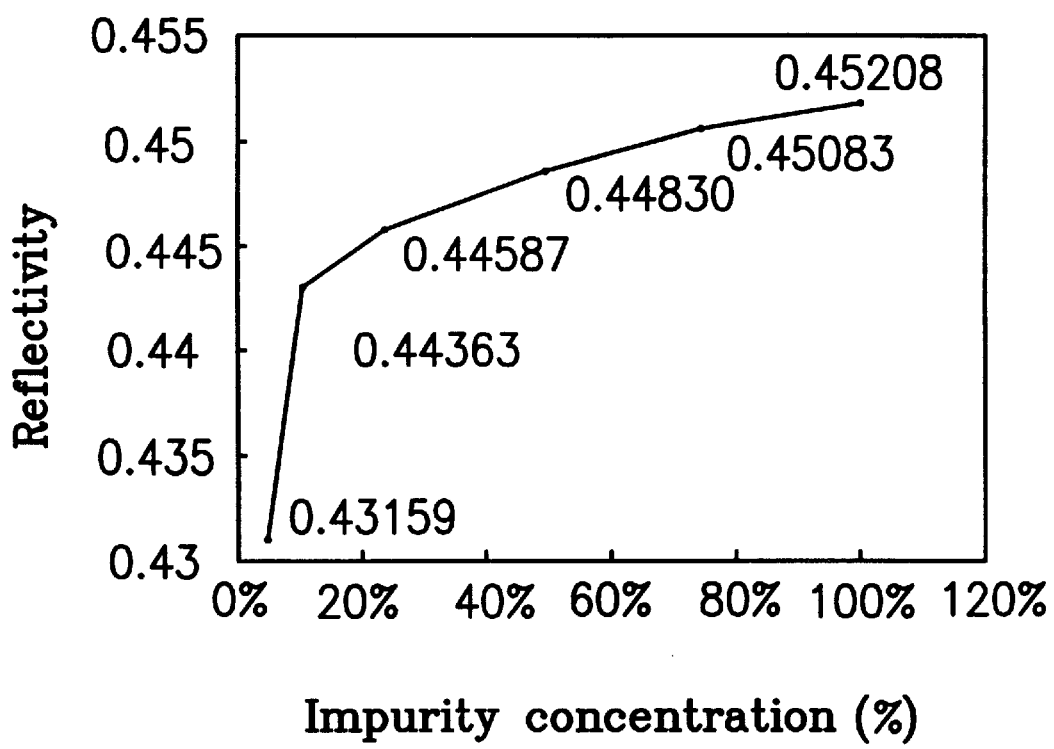
FIG. 3 is a graph, showing the reflectivity versus impurity dose characteristic of an impurity-doped polysilicon layer which is formed by a high-energy ion implantation process.

Based on the plot of FIG. 3, a high-energy doped polysilicon layer having an unknown impurity concentration can be determined by first measuring the reflectivity thereof, and then using mapping transformation on the plot of FIG. 3 to find the corresponding value of impurity concentration on the horizontal axis.

In conclusion, this method can be used to determine the impurity concentration of impurity-doped polysilicon layers that are formed by conducting the ion implantation process energy level 10 KeV to 120 KeV to add the impurity atoms to the crystal structure of the polysilicon layers with an impurity concentration of $1 \times 10^{11}$ to $5 \times 10^{16}$ atoms/cm².

The invention has been described using exemplary preferred embodiments. However, it is to be understood that the scope of the invention is not limited to the disclosed embodiments. To the contrary, it is intended to cover various modifications and similar arrangements. The scope of the claims, therefore, should be accorded the broadest interpretation so as to encompass all such modifications and similar arrangements.

TABLE 1

| Sample # (impurity-doped polysilicon) | TW value |
|---|---|
| 1 | 150,000 |
| 2 | 49,000 |
| 3 | 80,000 |

TABLE 1-continued

| Sample # (impurity-doped polysilicon) | TW value |
|---|---|
| 4 | 150,000 |
| 5 | 55,000 |

TABLE 2

| | Sample # | Reflectivity |
|---|---|---|
| Impurity-doped Polysilicon | 1 | 0.4868 |
| | 2 | 0.4856 |
| | 3 | 0.4848 |
| | 4 | 0.4861 |
| | 5 | 0.4851 |
| Undoped Polysilicon | 6 | 0.6317 |
| | 7 | 0.6290 |
| | 8 | 0.6339 |
| | 9 | 0.6267 |
| | 10 | 0.6332 |

TABLE 3

| Impurity Concentration | Reflectivity |
|---|---|
| 0% | 0.6249 |
| 25% | 0.5676 |
| 50% | 0.5303 |
| 75% | 0.5031 |
| 100% | 0.4889 |

TABLE 4

| Impurity Concentration | TW value | | |
|---|---|---|---|
| | Sample #1 | Sample #2 | Sample #3 |
| 0% | 26,732.4 | 27,165.9 | 27,838.3 |
| 5% | 8,021.3 | 7,686.8 | 11,127.6 |
| 10% | 8,534.4 | 9,297.2 | 11,053.3 |
| 25% | 35,003.5 | 35,021.4 | 34,656.2 |
| 50% | 50,518.3 | 48,657.4 | 47,102.2 |
| 75% | 57,085.7 | 56,525.8 | 53,815.7 |
| 100% | 60,666.0 | 62,056.3 | 57,374.8 |

TABLE 5

| Impurity Concentration | Reflectivity | | | |
|---|---|---|---|---|
| | Sample #1 | Sample #2 | Sample #3 | Average |
| 0% | 0.39907 | 0.39826 | 0.39783 | 0.39839 |
| 5% | 0.44568 | 0.44579 | 0.44571 | 0.44573 |
| 10% | 0.44877 | 0.44887 | 0.44878 | 0.44881 |
| 25% | 0.45042 | 0.45045 | 0.45049 | 0.45045 |
| 50% | 0.45218 | 0.45220 | 0.45225 | 0.45221 |
| 75% | 0.45297 | 0.45303 | 0.45306 | 0.45302 |
| 100% | 0.45322 | 0.45332 | 0.45331 | 0.45328 |

TABLE 6

| Impurity Concentration | TW value | | |
|---|---|---|---|
| | Sample #1 | Sample #2 | Sample #3 |
| 0% | 14,111.0 | 24,522.3 | 16,091.9 |
| 5% | 12,855.4 | 31,573.5 | 8,281.9 |
| 10% | 34,182.5 | 51,763.8 | 32,882.0 |

TABLE 6-continued

| Impurity Concentration | TW value | | |
|---|---|---|---|
| | Sample #1 | Sample #2 | Sample #3 |
| 25% | 30,993.8 | 45,127.8 | 26,915.3 |
| 50% | 24,288.1 | 41,256.7 | 22,871.8 |
| 75% | 20,568.0 | 34,492.4 | 19,142.9 |
| 100% | 17,400.9 | 33,546.8 | 17,562.0 |

TABLE 7

| Impurity Concentration | Reflectivity | | | |
|---|---|---|---|---|
| | Sample #1 | Sample #2 | Sample #3 | Average |
| 0% | 0.40226 | 0.40061 | 0.40268 | 0.40185 |
| 5% | 0.43186 | 0.43130 | 0.43160 | 0.43159 |
| 10% | 0.44373 | 0.44328 | 0.44387 | 0.44363 |
| 25% | 0.44600 | 0.44557 | 0.44603 | 0.44587 |
| 50% | 0.44840 | 0.44804 | 0.44846 | 0.44830 |
| 75% | 0.45089 | 0.45061 | 0.45099 | 0.45083 |
| 100% | 0.45211 | 0.45195 | 0.45219 | 0.45208 |

What is claimed is:

1. A method for inspecting an impurity-doped polysilicon layer having an unknown impurity concentration, comprising the steps of:

(1) preestablishing the reflectivity versus impurity concentration for the impurity-doped polysilicon layer, wherein the impurity-doped polysilicon layer is formed by conducting an ion implantation process at an energy of 10 KeV to 120 KeV to form an impurity concentration of $1 \times 10^{11}$ to $5 \times 10^{16}$ atoms/cm$^2$;

(2) illuminating the impurity-doped polysilicon layer;

(3) measuring the reflectivity value of the impurity-doped polysilicon layer; and (4) using a mapping transformation based on the preestablished reflectivity versus impurity concentration characteristic to find the corresponding value of the impurity concentration of the impurity-doped polysilicon layer based on the measured reflectivity value.

2. The method of claim 1, wherein the step of conducting includes doping a polysilicon layer by a low-energy ion implantation process.

3. The method of claim 1, wherein the step of conducting includes doping a polysilicon layer by an intermediate-energy ion implantation process.

4. The method of claim 1, wherein the step of conducting includes doping a polysilicon layer by a high-energy ion implantation process.

* * * * *